US008231657B2

(12) United States Patent
Eckhardt et al.

(10) Patent No.: US 8,231,657 B2
(45) Date of Patent: Jul. 31, 2012

(54) LOAD BEARING FLEXIBLE SPINAL CONNECTING ELEMENT

(75) Inventors: Jason John Eckhardt, Memphis, TN (US); Tom J. Francis, Cordova, TN (US); Hai H. Trieu, Cordova, TN (US)

(73) Assignee: Warsaw Orthopedic, Warsaw, IN (US)

( * ) Notice: Subject to any disclaimer, the term of this patent is extended or adjusted under 35 U.S.C. 154(b) by 79 days.

(21) Appl. No.: 12/852,658

(22) Filed: Aug. 9, 2010

(65) Prior Publication Data
US 2010/0298883 A1 Nov. 25, 2010

Related U.S. Application Data

(62) Division of application No. 11/429,818, filed on May 8, 2006, now Pat. No. 7,785,350.

(51) Int. Cl.
A61B 17/70 (2006.01)

(52) U.S. Cl. ........................................ 606/254

(58) Field of Classification Search .............. 606/60, 606/250, 254, 255, 259, 260, 264, 265, 279
See application file for complete search history.

(56) References Cited

U.S. PATENT DOCUMENTS

| | | | |
|---|---|---|---|
| 4,361,141 A | 11/1982 | Tanner | |
| 4,771,767 A | 9/1988 | Steffee | |
| 4,854,304 A | 8/1989 | Zielke | |
| 5,047,029 A * | 9/1991 | Aebi et al. | 606/264 |
| 5,154,718 A | 10/1992 | Cozad et al. | |
| 5,217,461 A | 6/1993 | Asher et al. | |
| 5,330,472 A | 7/1994 | Metz-Stavenhagen | |
| 5,330,474 A | 7/1994 | Lin | |
| 5,336,223 A | 8/1994 | Rogers | |
| 5,403,314 A | 4/1995 | Currier | |
| 5,425,732 A | 6/1995 | Ulrich | |
| 5,486,174 A | 1/1996 | Fournet-Fayard et al. | |
| 5,540,688 A | 7/1996 | Navas | |
| 5,562,660 A | 10/1996 | Grob | |
| 5,575,790 A | 11/1996 | Chen et al. | |
| 5,593,408 A | 1/1997 | Gayet et al. | |
| 5,630,816 A | 5/1997 | Kambin | |
| 5,704,936 A | 1/1998 | Mazel | |
| 6,099,528 A | 8/2000 | Saurat | |
| 6,102,912 A | 8/2000 | Cazin et al. | |
| 6,296,644 B1 | 10/2001 | Saurat et al. | |
| 6,802,844 B2 | 10/2004 | Ferree | |
| 7,655,025 B2 * | 2/2010 | Ritland | 606/258 |
| 7,854,752 B2 * | 12/2010 | Colleran et al. | 606/279 |
| 2002/0133155 A1 | 9/2002 | Ferree | |
| 2003/0093078 A1 | 5/2003 | Ritland | |
| 2003/0171749 A1 | 9/2003 | Le Couedic et al. | |
| 2004/0002708 A1 | 1/2004 | Ritland | |
| 2004/0049189 A1 | 3/2004 | Le Couedic et al. | |

(Continued)

FOREIGN PATENT DOCUMENTS

EP 0612507 A1 2/1994

(Continued)

Primary Examiner — Kevin T Truong
Assistant Examiner — Michael Araj

(57) ABSTRACT

Devices and methods for spinal stabilization include first and second anchor assemblies engageable to respective ones of first and second vertebrae and a connecting element engageable to the first and second anchor assemblies. The connecting element includes opposite first and second end members and a bumper assembly between the end members that flexibly connects the end members so the connecting element can provide dynamic stabilization of the spinal column when engaged to the anchor assemblies.

22 Claims, 6 Drawing Sheets

U.S. PATENT DOCUMENTS

| | | |
|---|---|---|
| 2004/0049190 A1 | 3/2004 | Biedermann et al. |
| 2004/0073215 A1 | 4/2004 | Cadi |
| 2004/0143264 A1 | 7/2004 | McAfee |
| 2004/0215191 A1 | 10/2004 | Kitchen |
| 2004/0215192 A1 | 10/2004 | Justis et al. |
| 2005/0010220 A1 | 1/2005 | Casutt et al. |
| 2005/0131407 A1 | 6/2005 | Sicvol et al. |
| 2005/0171540 A1 | 8/2005 | Lim et al. |
| 2005/0177156 A1 | 8/2005 | Timm et al. |
| 2005/0182401 A1 | 8/2005 | Timm et al. |
| 2005/0203514 A1 | 9/2005 | Jahng et al. |
| 2005/0203519 A1 | 9/2005 | Harms et al. |
| 2005/0261685 A1 | 11/2005 | Fortin et al. |
| 2005/0277922 A1 | 12/2005 | Trieu et al. |
| 2005/0288672 A1 | 12/2005 | Ferree |
| 2006/0009768 A1 | 1/2006 | Ritland |
| 2006/0036240 A1 | 2/2006 | Colleran et al. |
| 2006/0084994 A1 | 4/2006 | Atkinson et al. |
| 2006/0106381 A1 | 5/2006 | Ferree et al. |
| 2006/0149238 A1 | 7/2006 | Sherman et al. |

FOREIGN PATENT DOCUMENTS

| | | |
|---|---|---|
| WO | 0207622 A2 | 1/2002 |
| WO | 03007828 A1 | 1/2003 |
| WO | 2005110257 A1 | 11/2005 |

* cited by examiner

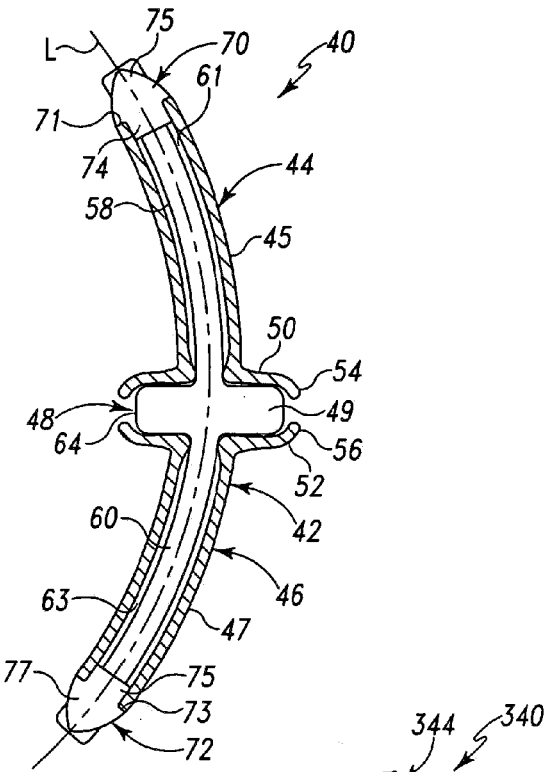
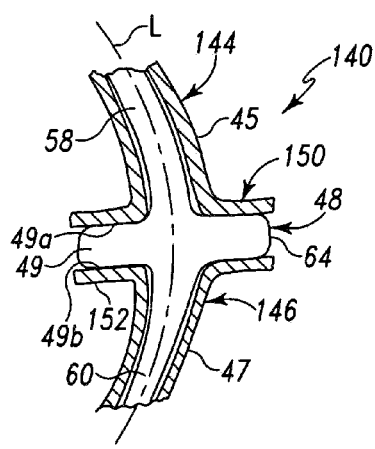
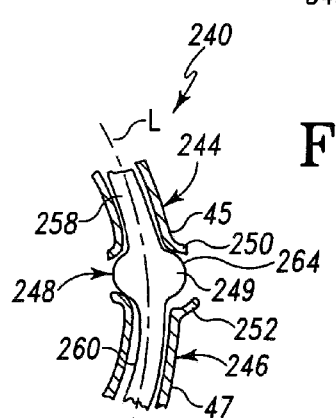
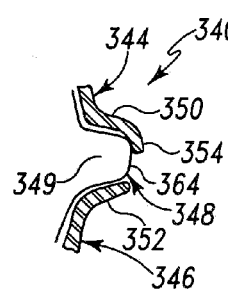
Fig. 2
Fig. 3
Fig. 4
Fig. 5

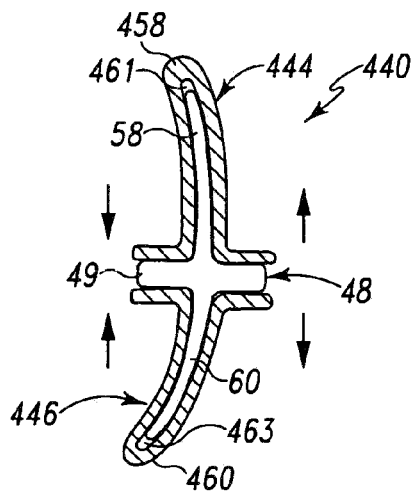
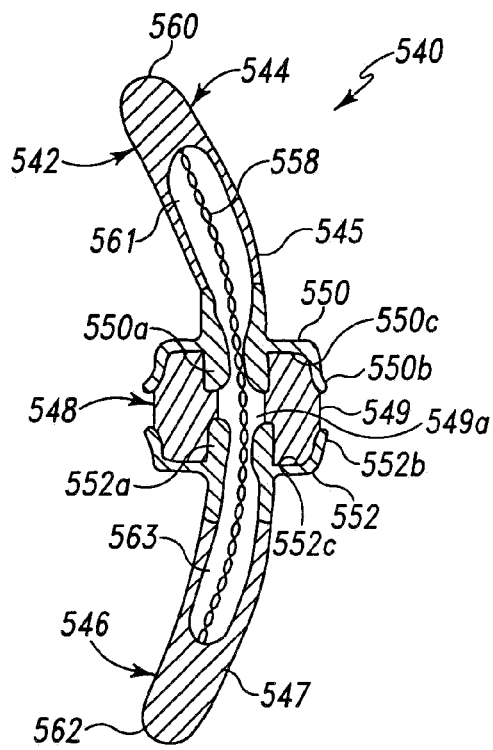
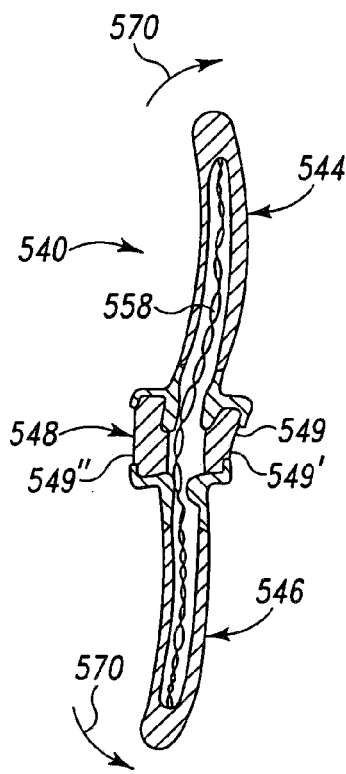
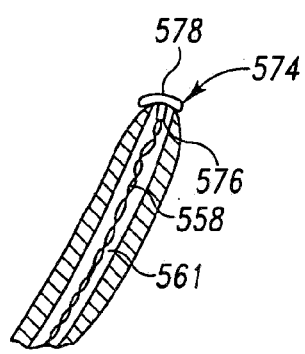
Fig. 6
Fig. 7
Fig. 8
Fig. 9

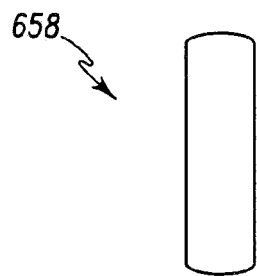
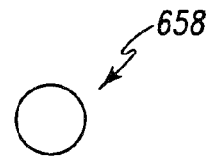
Fig. 18A　　Fig. 18B
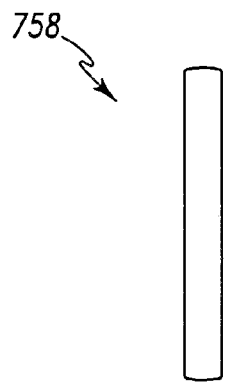
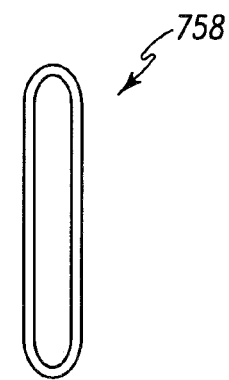
Fig. 19A　　Fig. 19B
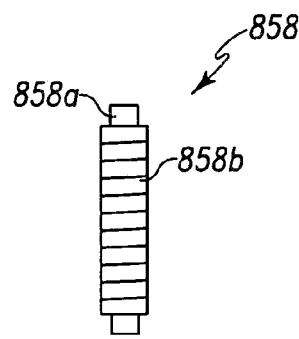
Fig. 20

LOAD BEARING FLEXIBLE SPINAL CONNECTING ELEMENT

BACKGROUND

Elongated connecting elements, such as rods, plates, tethers, wires, cables, and other devices have been implanted along the spinal column and connected between two or more anchors engaged between one or more spinal motion segments. Such connecting elements can provide a rigid construct that resists movement of the spinal motion segment in response to spinal loading or movement of the spinal motion segment by the patient. Still other connecting elements are flexible to permit at least limited spinal motion while providing resistance to loading and motion of the spinal motion segment. Such flexible connecting elements can be considered to provide dynamic spinal stabilization since at least limited movement of the spinal motion segment is preserved after implantation of the connecting element.

While prior connecting elements provide various spinal stabilization options, there remains a need for connecting elements that can provide dynamic resistance to forces and permit motion of the spinal column segment in different directions while maintaining stabilization of the spinal column segment and the structural integrity of the connecting element.

SUMMARY

The present invention generally relates to devices and methods for dynamically stabilizing a spinal column motion segment including at least two vertebrae by engaging a connecting element between the at least two vertebrae. The connecting element includes a pair of end members each having an elongated rod portion and a bumper assembly positioned between and flexibly connecting the end members to one another.

In one aspect a spinal stabilization system comprises first and second anchor assemblies engageable to respective ones of first and second vertebral bodies and an elongated connecting element including opposite first and second end members and a length along a longitudinal axis between the first and second end members sized for positioning between and engaging the first and second end members to each of the first and second anchor assemblies when the first and second anchor assemblies are engaged to the respective vertebral bodies. Each of the first and second end members includes an end wall and an axially extending rod portion extending from the respective end wall along the longitudinal axis in opposite directions from one another. The connecting element further includes a bumper assembly with a flexible bumper portion between the end walls of the first and second end members and flexible axial extensions extending in opposite directions from the bumper portion along the longitudinal axis and within axial bores of each of the rod portions of the first end second end members.

In another aspect, a spinal stabilization system comprises first and second anchor assemblies engageable to respective ones of first and second vertebral bodies and an elongated connecting element including opposite first and second end members and a length along a longitudinal axis between the first and second end members sized for positioning between and engaging each of the first and second anchor assemblies when the first and second anchor assemblies are engaged to the respective vertebral bodies. Each of the first and second end members includes an end wall and an axially extending rod portion extending from the respective end wall to an outer end opposite the end wall. The connecting element further includes a bumper assembly with a flexible bumper portion between the end members and a flexible linking element extending through an axial bore of each of the rod portions of the first and second end members. The linking element is engaged to the outer ends of each of the rod portions of the first and second end members.

In a further aspect, a connecting element for a dynamic spinal stabilization system includes an elongated body extending along a longitudinal axis that includes opposite first and second end members and a bumper portion between and flexibly supporting the first and second end members. The end members each include a rod portion extending along the longitudinal axis and an end wall at an end of the rod portion engaged with the bumper portion. At least one of the end walls includes an inner flange and an outer flange extending around the longitudinal axis and a space is formed between the inner and outer flanges with the bumper portion received in the space.

In yet another aspect, a connecting element for a dynamic spinal stabilization system includes a bumper assembly between a first end member and a second end member. The bumper assembly includes a cylindrical bumper portion and a first axial extension extending along a longitudinal axis in a first direction from the bumper portion and a second axial extension extending along the longitudinal axis in a second direction from the bumper portion opposite the first direction. The bumper portion extends outwardly from each of the first and second axial extensions. The first and second end members each include an end wall engaged to the bumper portion on opposite sides of the bumper portion. The end walls extend outwardly about respective rod portions with the respective rod portions extending along the longitudinal axis from the respective end wall and including an axial bore for receiving the respective axial extension of the bumper assembly.

According to another aspect, a method for assembling a connecting element for stabilizing a spinal column segment comprises: providing a first end member with a first rod portion and a first end wall at an end of the first rod portion, the first rod portion including a bore extending therealong that opens at the first end wall; providing a second end member with a second rod portion and a second end wall at an end of the second rod portion, the second rod portion including a bore extending therealong that opens at the second end wall; positioning the first rod portion and the second rod portion along respective ones of first and second axial extensions of a bumper assembly until the first and second end walls engage a bumper portion between the first and second axial extensions and an end of each of the axial extensions remote from the bumper portion is positioned adjacent a respective outer end of the first and second rod portions remote from the corresponding end wall of the respective rod portion; and pivoting the first and second end members relative to one another by compressing the bumper portion between the first and second end walls and flexing at least one of the first and second axial extensions relative to the bumper portion.

According to yet another aspect, a method for assembling a connecting element for stabilizing a spinal column segment includes: providing a first end member with a first rod portion and a first end wall at an end of the first rod portion, the first rod portion including a bore extending therealong that opens at the first end wall; providing a second end member with a second rod portion and a second end wall at an end of the second rod portion, the second rod portion including a bore extending therealong that opens at the second end wall; providing a bumper assembly including a bumper portion with a central bore extending between opposite end faces of the bumper portion and a linking element extending through the central bore; and positioning the linking element in the axial bores of each of the first and second rod portions and engaging the linking element to each of the first and second rod portions with the first and second end walls engaging the opposite end faces of the bumper portion and the rod portions lying along a longitudinal axis.

These and other aspects will be discussed further below.

BRIEF DESCRIPTION OF THE DRAWINGS

FIG. 2 is an elevation view in partial longitudinal section of one embodiment connecting element of the spinal implant system of FIG. 1.

FIG. 3 is an elevation view in partial longitudinal section of a mid-portion of another embodiment connecting element.

FIG. 4 is an elevation view in partial longitudinal section of a mid-portion of another embodiment connecting element.

FIG. 5 is an elevation view in partial longitudinal section of part of a mid-portion of another embodiment connecting element.

FIG. 6 is an elevation view in partial section of another embodiment connecting element of the spinal implant system of FIG. 1.

FIG. 7 is an elevation view in partial longitudinal section of another embodiment connecting element of the spinal implant system of FIG. 1 in an un-flexed or neutral condition.

FIG. 8 is the connecting element of FIG. 7 in a flexed condition.

FIG. 9 is an elevation view of a portion of a longitudinal section of an end member of another embodiment connecting element.

FIGS. 18A and 18B are an elevation view and an end view, respectively, of another embodiment linking element.

FIGS. 19A and 19B are first and second elevation views, respectively, rotated 90 degrees relative to one another about the longitudinal axis of the linking element.

FIG. 20 is an elevation view of another embodiment linking element.

DESCRIPTION OF THE ILLUSTRATED EMBODIMENTS

Figure 1:
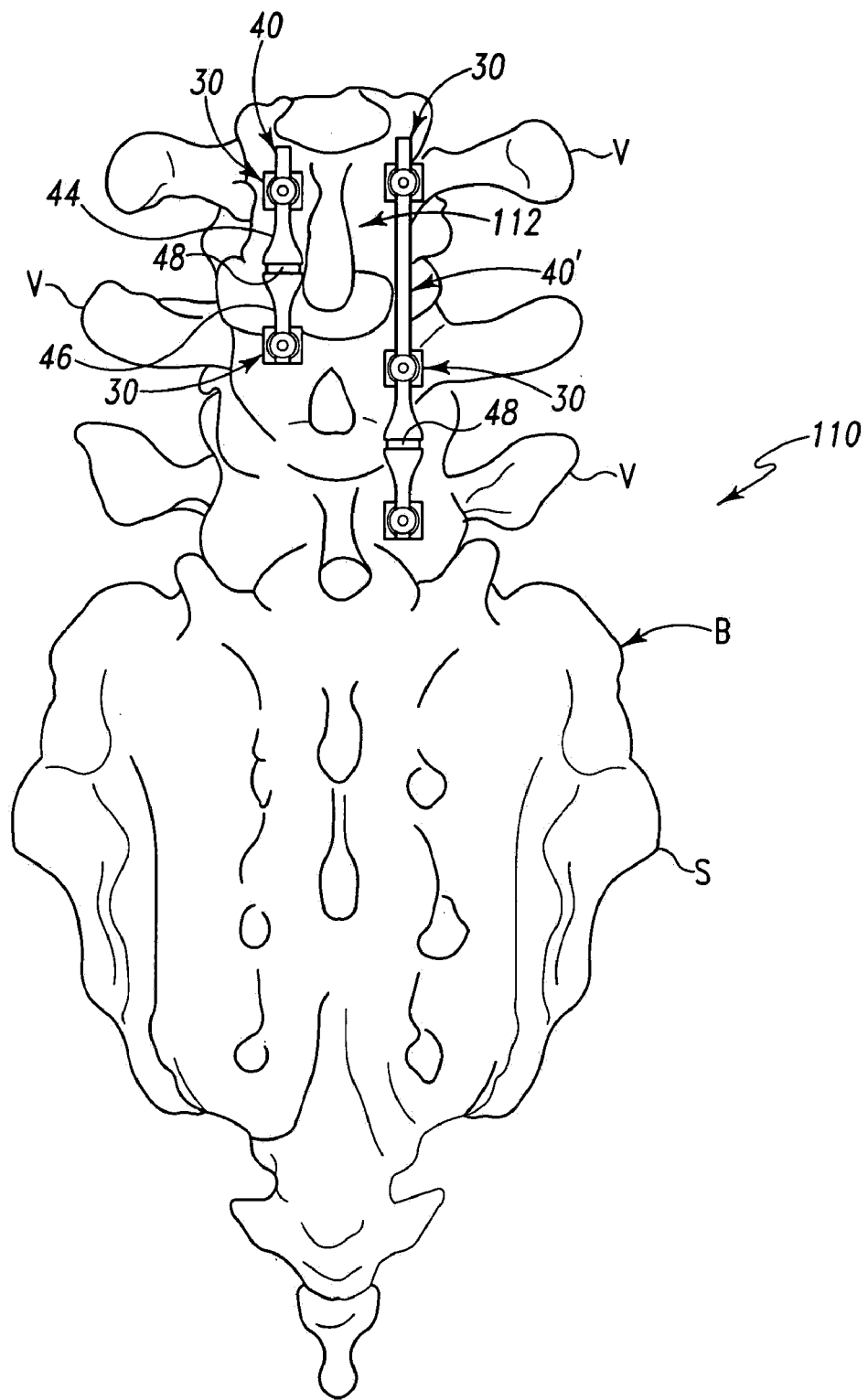
FIG. 1 is a posterior elevation view of a spinal column segment and spinal implant system.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

Devices and methods for providing dynamic stabilization of one or more spinal motion segments are provided. The devices and methods include a connecting element between two or more bone anchor assemblies that can be engaged to at least two or more vertebral bodies of a spinal motion segment. The connecting element extends along a longitudinal axis and includes opposing end members with rod portions at each end engageable to respective ones of the anchor assemblies and a bumper assembly between the end members that allows movement of the vertebrae to which the connecting element is attached. The end members can be configured to interfit with the bumper assembly to provide a stabilization construct that is movable in response to at least spinal extension, spinal flexion and lateral bending of the spinal column. The bumper assembly defines multiple planes and locations of motion relative to the longitudinal axis of the connecting element while providing appropriate stiffness for spinal stabilization as the spinal motion segment deviates from the neutral position.

The bumper assembly can be an integral construct with a bumper portion between the end members and axial extensions extending in opposite directions from the bumper portion and into one or both of the end members along the longitudinal axis of the connecting element. The bumper portion and axial extensions can be flexible and resilient to resist spinal motion while allowing the connecting element to return toward a neutral position with the spinal motion segment. In other embodiments, the bumper assembly includes a linking element extending through or from a bumper portion between the end members. The linking element extends axially into the end members and is engaged thereto to flexibly link the opposite ends of the end members to one another. The linking element can be structured to dynamically resist tension loading while the bumper portion positioned between the end members is structured to dynamically resist at least compression loading. The bumper assembly can be housed at least partially within the end members. The connecting element can be curved along the longitudinal axis, linear along the longitudinal axis, or include some other non-linear form.

The anchor assemblies discussed herein can be multi-axial or uni-axial in form, and can include an anchor member engageable to a vertebral body and a receiver, post or other device for receiving or engaging a respective end member of the connecting element. The multi-axial anchor assemblies allow the anchor member to be positioned at various angles relative to the connecting element engaging portion of the anchor assembly. The uni-axial anchor assemblies can also provide a fixed positioning of the connecting element engaging portion to the anchor member. The anchor member of the anchor assemblies can form a distal lower portion that is engageable to a vertebral body with the proximal connecting element engaging portion positioned adjacent the vertebral body. In one embodiment, the anchor member is in the form of a bone screw with a threaded shaft and a proximal head that is pivotally captured in the receiver. In other embodiments, the distal anchor member can be in the form of a hook, staple, cable, tether, suture anchor, interbody fusion implant, artificial disc implant, bolt, or other structure engageable to bony tissue. The implant engaging portion can include a receiver with a U-shape, O-shape, or other shape that defines a passage that receives the respective end member of the connecting element therein, thereon, therethrough, or thereover, for example. The connecting element can extend from one or both of the anchor assemblies for securement to one or more additional vertebral bodies.

FIG. 1 illustrates a posterior spinal implant system 110 located along a spinal column of a patient. More specifically, implant system 110 can be affixed to bones B of the spinal column segment 112 from a posterior approach, although application in posterior-lateral, lateral, antero-lateral and anterior approaches, for example, are also contemplated. Bones B can include the sacrum S and several vertebral bodies V. Implant system 110 generally includes several bone anchor assemblies 30 and elongated connecting elements 40 and/or 40' structured to selectively interconnect with bone anchor assemblies 30. Connecting elements 40 may have a bumper assembly 48 between end members 44, 46 and an overall length sized to extend between bone anchor assemblies 30 engaged to least two vertebral bodies V. Connecting element 40' has a length sized to extend along three or more vertebrae with at least one bumper assembly 48 between adjacent vertebrae. The portions of connecting element 40' extending between the other vertebrae may include a bumper assembly or may include a rod portion that provides rigid or dynamic stabilization with or without a bumper assembly.

In implant system 110, bone anchor assemblies 30 are affixed to various locations of the spinal column segment 112, such as the pedicles, and interconnected with one or more connecting elements 40, 40'. Other procedures contemplate implant system 110 may be employed at other locations about the spinal column, including anterior, antero-lateral, and lateral locations. Implant system 110 may also be employed in procedures where such locations are combined; e.g. to provide posterior and anterior stabilization. Implant system 110 may be used for, but is not limited to, treatment of degenerative spondylolisthesis, herniation, degeneration, arthritis, fracture, dislocation, scoliosis, kyphosis, spinal tumor, and/or a failed previous fusion.

FIG. 2 shows an elevation view of one embodiment of connecting element 40, it being understood that connecting element 40' could be similarly configured albeit with a length to extend between three or more vertebrae as discussed above. Connecting element 40 includes a body 42 extending along a longitudinal axis L between a first end member 44 and an opposite second end member 46. A bumper assembly 48 extends within and flexibly connects end members 44, 46. Bumper assembly 48 includes a bumper portion 49 situated between and abuttingly engaging end members 44, 46. Bumper assembly 48 further includes first and second axial extensions 58, 60 extending axially from and in opposite directions from bumper portion 49 within the respective rod portions 45, 47. Rod portions 45, 47 can each define an axial bore 61, 63 extending therethrough to receive the respective axial extension 58, 60. Axial extensions 58, 60 can occupy all or substantially all of the axial bores 61, 63 to provide form fitting engagement with the respective rod portion 45, 47.

End members 44, 46 can be configured to be engaged to a respective one of the bone anchor assemblies 30 and further configured to be engaged with bumper assembly 48 therebetween and therein. In one embodiment, end members 44, 46 have rod portions 45, 47, respectively, along longitudinal axis L that are in the form of and sized and shaped with a cross-section suitable for a spinal rod system for positioning and implantation along the spinal column of a human patient. In another embodiment, rod portions 45, 47 are each sized with a length along longitudinal axis L that extends from bumper portion 49 of bumper assembly 48 and engages an anchor assembly engaged to an adjacent vertebra.

In another embodiment, one or both of the rod portions 45, 47 has a length along longitudinal axis L that extends between two or more anchor assemblies engaged to two or more adjacent vertebrae, such as shown with connecting element 40'. In such multi-level embodiments, the respective end member 44, 46 can include a cross-section that is constant between adjacent anchor assemblies, or that includes another bumper assembly 48 between anchor assemblies.

Bumper portion 49 of bumper assembly 48 in FIGS. 2 and 3 can include a cylindrical type shape with flat or planar upper and lower faces 49a, 49b and a sidewall 64 that can be linear, convexly curved, or concavely curved between the upper and lower faces 49a, 49b of bumper portion 49. Other embodiments contemplate that faces 49a, 49b can be concavely curved, convexly curved, or include some other shape or form. Faces 49a, 49b can also be configured differently from one another.

Each of the end members 44, 46 further includes an end wall 50, 52, respectively, at an end thereof opposite the respective rod portion 45, 47. End walls 50, 52 can each extend outwardly or radially outwardly from the rod portion to provide an enlarged mid-portion about longitudinal axis L to house or engage bumper portion 49 of bumper assembly 48. The outer edge or perimeter of the end walls 50, 52 can include a flange 54, 56 extending thereabout and in the general direction of longitudinal axis L toward the other end wall 50, 52. The flanges 54, 56 can cup or radially restrain or constrain bumper portion 49 between end members 44, 46. The inner contact surfaces of flanges 54, 56 can be smooth and rounded to minimize the potential for wear of bumper portion 49 as rod portions 45, 47 and end walls 50, 52 move relative to bumper portion 49 in response to motion of the spinal segment.

Other embodiments contemplate other arrangements for the end members. For example, FIG. 3 shows a connecting element 140 with end members 144, 146 that are similar to end members 44, 46. However, end walls 150, 152 do not include any flange extending thereabout. Rather, the outer perimeter of end walls 150, 152 defines a disc shape that does not axially overlap with the sidewall 64 of bumper portion 49. Accordingly, the frictional wear and tear of bumper portion 49 by rod portions 144, 146 is minimized, and bumper portion 49 is not radially constrained by end walls 150, 152.

In FIG. 4 there is shown connecting element 240 that is similar to connecting element 40. However, bumper assembly 248 includes a bumper portion 249 having an outer surface 264 defining a bulbous or spherical type shape. End members 244, 246 include end walls 250, 252 that have concavely curved inner surface and convexly curved outer surfaces to conform about the spherical bumper portion 249. Axial extensions 258, 260 extend from bumper portion 249 in opposite directions along longitudinal axis L.

It is also contemplated that the end walls of the end members need not be arranged identically. For example, FIG. 5 shows a portion of a connecting element 340 that is similar to connecting element 40. Connecting element 340 includes bumper assembly 348 with a bumper portion 349 and end members 344, 346 with end walls 350, 352. End wall 350 includes a flange 354 extending from the outer perimeter thereof toward the other end wall 352 and along a portion of outer surface 364 of bumper portion 349. End wall 352, on the other hand, does not include a flange extending along outer surface 364. The reverse arrangement is also contemplated where end wall 350 does not include a flange but end wall 352 does. In still other embodiments, a flange could be provided that axially overlaps the other end wall. In yet another embodiment, each end wall could be provided with a flange that axially overlaps the flange of the other end wall.

Referring back to FIG. 2, bumper assembly 48 and the other bumper assembly embodiments can be provided in the form of a one piece flexible member that provides a shock absorbing effect in transmitting spinal column loads between the anchor assemblies 30 to which it is engaged and also a variable resistance to spinal motion in flexion, extension and lateral bending. Axial extensions 58, 60 could be formed integrally with bumper portion 49 or secured thereto with adhesives, fasteners, fusing techniques, or bonding agents, for example. In another embodiment, bumper portion 49 includes a central bore and axial extensions are formed as a single piece positioned through the central bore and extending axially in opposite directions therefrom.

The flexibility of the axial extensions 58, 60 extending along all or a substantial portion of the length of the rod portions 45, 47 allows dynamic resistance along a substantial portion of the length of body 42 without relying solely or primarily on a hinge effect at the intermediate portion between the end members 44, 46. The rod portions 45, 47 can have a rigid body structure extending about the axial extensions 58, 60 to facilitate secure engagement of the connecting element to the anchor assemblies. Rigid rod portions 45, 47 can also facilitate percutaneous insertion of connecting element 40. Connecting element 40 can also be inserted and engaged to anchor assemblies 30 in open procedures where the skin and tissue between the anchor assemblies is cut and retracted to allow connecting element placement between the anchor assemblies through the retracted opening.

Various embodiments of connecting element 40 contemplate various techniques for securing end members 44, 46 to axial extensions 58, 60. In FIG. 2, the ends of rod portions 45, 47 include constraining members 70, 72, respectively. Constraining members 70, 72 can be engaged to a corresponding outer end of axial extensions 58, 60 and protrude outwardly from the respective rod portion 45, 47. Constraining members 70, 72 include inner sleeves 74, 75, respectively positioned in respective ones of the axial bores 61, 63 opening at the outer ends of rod portions 45, 47 remote from the corresponding end walls 50, 52. A lip 71 of constraining member 70 and a lip 73 of constraining member 72 can abuttingly engage the respective end of the rod portions 45, 47. The ends of rod portions 45, 47 can be crimped, fastened or otherwise secured to inner sleeves 74, 75 of constraining members 70, 72 to axially retain constraining members 70, 72 thereon. Alternatively, outer sleeves 75, 77 of constraining members 70, 72 could be crimped about the portion of the axial extension 58, 60 extending therethrough.

In another embodiment, connecting element 440 shown in FIG. 6 includes end members 444, 446 similar to end members 44, 46. However, end members 444, 446 include closed end portions 458, 460, respectively, where the rod portion provides an integral tip that closes the outer ends of the bores 461, 463 defined by end members 444, 446 remote from the end walls. Axial bores 461, 463 receive axial extensions 58, 60 of bumper assembly 48. Axial extensions 58, 60 can axially float in bores 461, 463 of end members 444, 446, or axial extensions 58, 60 could be secured thereto with an adhesive, bonding process, frictional fit, or fasteners, for example. Axial extensions 58, 60 could also be injection molded for positioning in bores 461, 463.

Referring now to FIG. 7, there is shown another embodiment connecting element 540 with a body 542 including a first end member 544 and a second end member 546. First end member 544 includes a rod portion 545 and an end wall 550. Second end member 546 includes a rod portion 547 and an end wall 552. Connecting element 540 further includes a bumper assembly 548 with a bumper portion 549 between end members 544, 546 and a linking element 558 extending through or from bumper portion 549 and between the ends of rod portions 545, 547 within axial bores 561, 563 defined by the end members 544, 546. Linking element 558 can be in the form of a tether such as a strand, cord, rope, suture, wire, braid or other structure that collapses in response to longitudinal compression forces yet is sufficiently strong to resist axial tension forces that may tend to pull end members 544, 546 away from one another and away from bumper portion 549.

End walls 550, 552 can include a structure that radially constrains and captures bumper portion 549 therebetween. For example, end wall 550 can include an inner flange 550a and an outer flange 550b, and end wall 552 can include an inner flange 552a and an outer flange 552b. The inner and outer flanges 550a, 550b define space 550c therebetween, and the inner and outer flanges 552a, 552b define space 552c therebetween. Bumper portion 549 can include a donut shape that fits within spaces 550c, 552c between the inner and outer flanges of each of the end walls 550, 552.

End walls 550, 552 can be integral with rod portions 545, 547, or formed as a separate component and slip fit and welded to the respective rod portions as shown. In another embodiment, only one of the end walls 550, 552 includes inner and outer flanges. The other end wall could include a single inner flange, a single outer flange, or no flange.

Linking element 558 can extend through the central bore 549a defined by bumper portion 549. The ends of linking element 558 are secured to respective ones of the rod portions 545, 547 at closed outer ends 560, 562 of rod portions 545, 547, respectively. Linking element 558 can be molded into, fastened, welded, fused or otherwise secured to end members 544, 546. Linking element 558 can be pre-tensioned to provide a bias that tends to compress bumper portion 549 between end walls 550, 552 and maintain end members 544, 546 in contact therewith, although non pre-tensioned embodiments are also contemplated.

In another embodiment shown in FIG. 9, bore 561 extends through and opens at the outer end of the rod portion (only one shown). The respective end of linking element 558 is engaged to constraining member 574. Constraining member 574 can include a post 576 extending into bore 561 and engaged with an end of linking element 558. Constraining member 574 can also include an enlarged head 578 in abutting engagement with the respective adjacent end of the rod portion.

Linking element 558 can resist tension forces and also bending forces by flexibly limiting or restraining movement of the outer ends of end members 544, 546 relative to one another. For example, as shown in FIG. 8, connecting element 540 is flexed as indicated by arrows 570. One side 549' of bumper portion 549 is compressed in response to the flexing while the opposite side 549" is tensioned or in a neutral state. Linking element 558 can stretch to allow movement of the rod portions 545, 547 away from one another. In another embodiment, linking element 558 does not stretch, or reaches a stretching limit under spinal loading, to effectively limit movement of the rod portions 545, 547 away from one another. When the spinal loading is removed, bumper portion 549 can resiliently return toward a neutral state such as shown in FIG. 7.

Figure 10:
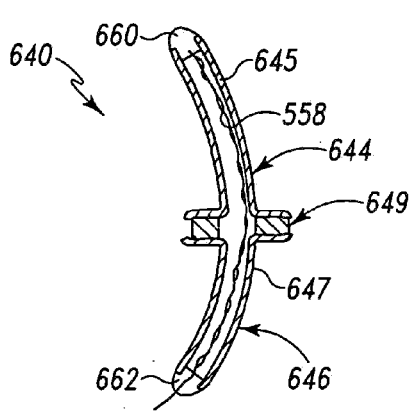
FIG. 10 is an elevation view in partial longitudinal section of another embodiment connecting element.

FIG. 10 shows another embodiment connecting element 640 that is similar to connecting element 540. However, the ends of the linking element 558 are positioned in or engaged to constraining members 660, 662 at the ends of the rod portions 645, 647 of end members 644, 646. The rod portions 645, 647 can each define an open outer end along the longitudinal axis to facilitate placement of the respective constraining member 660, 662 therein. Constraining members 660, 662 can be crimped to the respective adjacent end of linking element 558 and secured to the end of the respective rod portion 645, 647 in any suitable manner.

Figure 11:
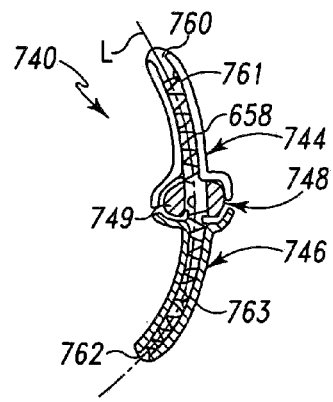
FIG. 11 is an elevation view in partial longitudinal section of another embodiment connecting element.

Referring now to FIG. 11, there is shown another embodiment connecting element 740 having end members 744, 746 lying along a longitudinal axis L. End members 744, 746 can define axial bores 761, 763 therealong. Connecting element 740 can also include a bumper assembly 748 having a bumper portion 749 and a linking element 658. Bumper portion 649 can include a central bore to form a donut shape, and linking element 658 can extend through the central bore and through axial bores 661, 663 of end members 744, 746. Linking element 658 can be comprised of an injection molded or otherwise formed material within axial bores 661, 663 and through the central bore of bumper portion 749. Linking element 658 can occupy substantially all the space defined by bores 761, 763. The ends of bores 761, 763 can be closed or sealed with an end cap or other structure, or can remain open.

Figure 12:
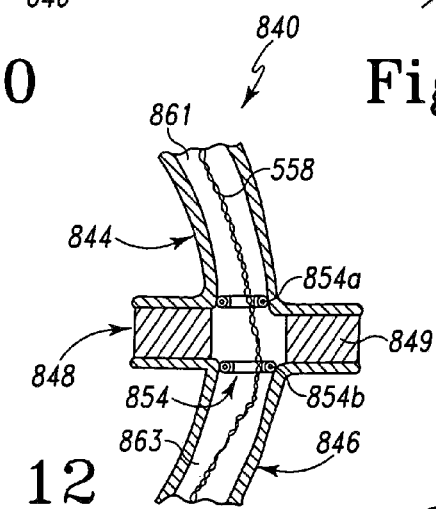
FIG. 12 is an elevation view in partial longitudinal section of a mid-portion of another embodiment connecting element.
Figure 13:
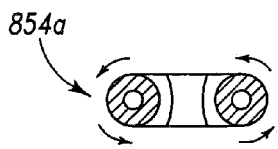
FIG. 13 is a section view of a rotation member of the connecting element of FIG. 12.

Referring now to FIG. 12, there is shown a portion of another embodiment connecting element 840. Connecting element 840 includes end members 844, 846 and a bumper assembly 848 extending therebetween. Bumper assembly 848 includes a bumper portion 849 and linking element 558 extending through a central bore of bumper portion 849. Bumper assembly 848 further includes a rotating component 854 within axial bores 861, 863 of end members 844, 846. Linking element 558 can extend through rotating component 854. Rotating component 854 can include rollers 854a, 854b through which linking element 558 extends. Rollers 854a, 854b, one of which is shown in isolation in FIG. 13, can maintain linking element 858 in a desired position or condition as end members 844, 846 flex and rotate relative to one another as a result of spinal extension, flexion or lateral bending. The rollers can rotate along or about linking element 558 to facilitate linking element 558 moving relative thereto without causing the linking element to bind, kink or twisting as a result of such bending and other movement.

Figure 14:
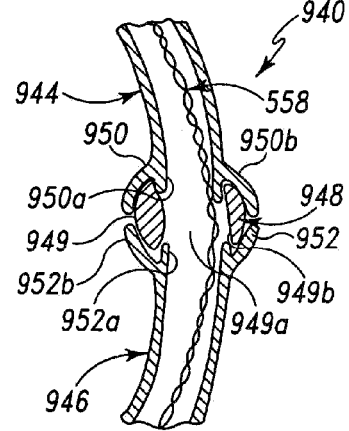
FIG. 14 is an elevation view in partial longitudinal section of a mid-portion of another embodiment connecting element.

Referring now to FIG. 14 there is shown a portion of another embodiment connecting element 940 that is similar to connecting element 540 discussed above. Connecting element 940 includes end members 944, 946 and a bumper assembly 948 with a bumper portion 949 and a linking element 558. Bumper portion 949 includes a donut type shape with a wall 949b extending around central bore 949a that is tapered toward the opposite ends thereof to facilitate articulation of the ends members 944, 946 about the ends of the bumper portion 949. To maintain engagement of the end members 944, 946 to bumper portion 949, end members 944, 946 can include end walls 950, 952, respectively, that include inner flanges 950a, 952a and outer flanges 950b, 952b that sandwich bumper portion 949 therebetween. The inner flanges 950a, 952a and outer flanges 950b, 952b can be contoured to conform to the respective outer surface profile of the bumper portion 949.

Figure 15:
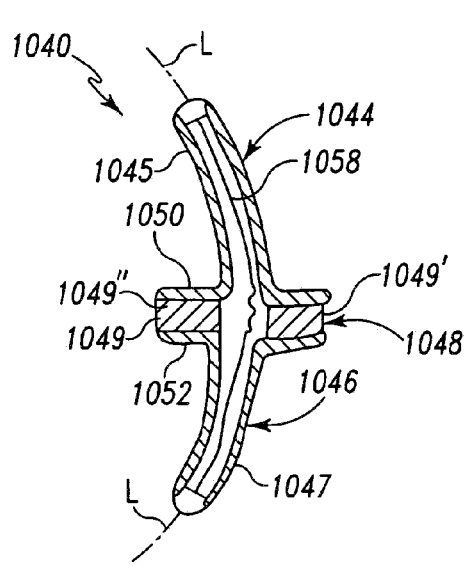
FIG. 15 is an elevation view in partial longitudinal section of another embodiment connecting element.

Referring now to FIG. 15, there is shown another embodiment connecting element 1040. Connecting element 1040 includes end members 1044, 1046 and bumper assembly 1048 along longitudinal axis L. Bumper assembly 1048 includes a bumper portion 1049 between end members 1044, 1046 and a linking element 1058 extending between and connecting rod portions 1045, 1047 of end members 1044, 1046 a location at or adjacent the outer ends thereof. Linking element 1058 can be a cord, strand or other device that is slack along longitudinal axis L when connecting element 1040 is in the neutral condition, as shown in FIG. 15. When connecting element 1040 is flexed, linking element 1058 can tension when sufficient displacement has occurred. Linking element can be inelastic so that a limit to the displacement is provided upon tensioning of the linking element.

In one embodiment, bumper portion 1049 is adhered to end walls 1050, 1502 of end members 1044, 1046 along one side 1049' while the opposite side 1049" can freely separate from one or both of end members 1044, 1046 when end members 1044, 1046 are tensioned or flexed. Linking element 1058 effectively maintains end members 1044, 1046 in an assembled condition with bumper portion 1049 by limiting the separation of end members 1044, 1046 when flexed.

Figure 16:
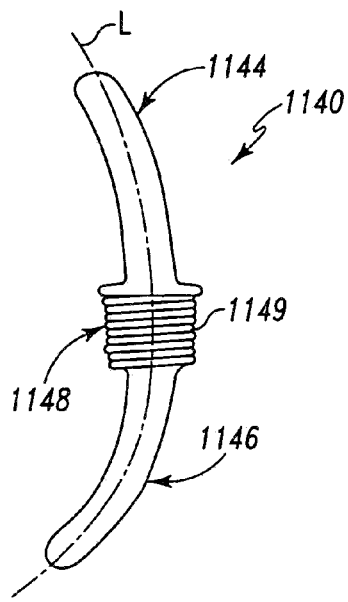
FIG. 16 is an elevation view of another embodiment connecting element.

FIG. 16 shows another embodiment connecting element 1140 having first and second end members lying 1144, 1146 along longitudinal axis L. End members 1144, 1146 are connected with a bumper assembly 1148 in the form of an external spring 1149. Spring 1149 can lengthen and shorten along longitudinal axis L in response to axial tension and compression loading, respectively. Furthermore, one side of spring 1149 can lengthen while the opposite side shortens in response to bending forces created by flexion, extension and lateral bending of the spinal motion segment. In yet another embodiment, bumper assembly 1148 is not a spring, but rather an accordion-like structure that is biased in neither tension nor compression, but rather folds and unfolds in response to lengthening and shortening of the space between end members 1144, 1146 caused by relative movement of the anchor assemblies to which the end members are attached.

Figure 17:
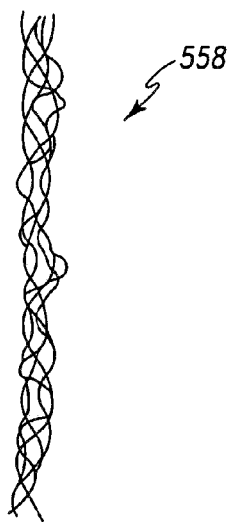
FIG. 17 is an elevation view of one embodiment linking element.

FIG. 17 shows an embodiment of linking element 558 in isolation. The linking element 558 can include a body that is comprised of woven strands of material to provide strength and resilience. Examples of suitable material include polyolefin, purcil, and bionate, to name a few. The body can also be in the form of a wire, rope, cord, band, belt, suture, bar, rod, mesh, fabric, or other suitable form.

In another example, FIGS. 18A-18B show a linking element 658 having a rod-like elongated body with a circular cross-sectional shape along its length. Linking element 658 can be flexible and elastic to facilitate spinal motion while providing adequate resistance to displacement forces to maintain spinal stabilization. FIGS. 19A and 19B show side views of a linking element 758 that includes a body in the structure of a band that forms a continuous loop. The ends of the band can be secured to end members of a connecting element to maintain compression on a bumper portion between the end members. The band can also stretch and resiliently return toward a non-stretched shape to maintain the configuration of the connecting element in the neutral state when the spinal bending loading is removed from the connecting element. FIG. 20 shows a linking element 858 that includes at least one inner strand 858a and at least one outer strand 858b wrapped therearound between the ends like a noose. The ends of the noose-like body can be secured to end members of a connecting element.

The linking elements can provide the connecting element with a stiffness that provides more resistance to spinal motion that creates axial tension loading without resisting or hindering spinal motion that results in axial compression loading, although it is contemplated that some compression loading resistance provided by the linking element is not precluded. Accordingly, spinal motion can be preserved while more effectively limiting tension or movement of the adjacent vertebral bodies away from one another while maintaining the connecting element as a functioning unit and resisting separation of one or both of the end members from the bumper portion therebetween.

The end members and/or linking elements can be made from nitinol, titanium, stainless steel, or other biocompatible metals and alloys thereof. The end members and/or linking elements can also be made from PEEK or other polymer material that is biocompatible. The linking element can be made from a material that is the same as or that differs from the material of the end members. The linking element can be a rod, cord, rope, wire, tether, belt, band, ribbon, braid, suture, bar, sleeve, tube, or include any other suitable form. The bumper portion and embodiments where the bumper portion includes axial extensions can be made from any suitable biocompatible material that is flexible and resilient to permit movement of the spinal motion segment to which it is attached while providing a desired stabilization effect. Rubbers, elastomers, and other materials can be employed for the bumper portion and axial extensions. The bumper portions and/or axial extensions can be injection molded, fabricated from stock material, or formed in situ with the end members.

While the invention has been illustrated and described in detail in the drawings and foregoing description, the same is to be considered as illustrative and not restrictive in character, it being understood that all changes and modifications that come within the spirit of the invention are desired to be protected.

What is claimed is:

1. A spinal stabilization system, comprising:
   first and second anchor assemblies engageable to respective ones of first and second vertebral bodies; and
   an elongated connecting element including opposite first and second end members and a length along a longitudinal axis between said first and second end members sized for positioning between and engaging each of said first and second anchor assemblies when said first and second anchor assemblies are engaged to the respective vertebral bodies, wherein each of said first and second end members includes an end wall and an axially extending rod portion extending from said respective end wall to an outer end opposite said end wall, said connecting element further including a bumper assembly with a flexible bumper portion between said end members and a flexible linking element extending through an axial bore of each of said rod portions of said first and second end members, said linking element being engaged to said outer ends of each of said rod portions of said first and second end members, said bumper portion including a side face extending between opposite end faces, said end walls engaging said end faces and overlapping at least a portion of said side face.

2. The system of claim 1, wherein said bumper portion includes a central bore along said longitudinal axis and said linking element extends through said central bore.

3. The system of claim 1, wherein rod portions and said axial bores thereof are curved along said longitudinal axis.

4. The system of claim 1, wherein said linking element is structured to collapse in response to compression forces applied longitudinally thereto.

5. The system of claim 1, wherein said linking element includes a woven body structure.

6. The system of claim 1, wherein said linking element includes a body structure that forms a loop between opposite ends of said linking element.

7. The system of claim 1, wherein said linking element includes a body structure that includes at least one first axially extending strand and at least one second strand wrapped around said first strand between opposite ends of said first strand.

8. The system of claim 1, wherein said bumper portion includes a cylindrical shape with a central bore opening at said opposite end faces of said bumper portion and said linking element extends through said central bore.

9. The system of claim 8, wherein said bumper portion includes a wall about said central bore that tapers in width toward each of said end faces.

10. The system of claim 1, wherein said end walls each extend radially outwardly from said respective rod portion, each of said end walls including an inner flange and an outer flange, said inner and outer flanges extending around said longitudinal axis and extending generally in the direction of said longitudinal axis, said inner and outer flanges defining a space therebetween and said bumper portion is received in said space.

11. The system of claim 1, wherein said linking element is slack when said connecting element is in a neutral, unflexed condition.

12. The system of claim 11, wherein said linking element is inelastic.

13. The system of claim 1, further comprising at least one roller in at least one of said rod portions adjacent said bumper portion, said linking element extending through said roller.

14. A connecting element for a dynamic spinal stabilization system, comprising:
   an elongated body extending along a longitudinal axis and including opposite first and second end members and a bumper portion between and flexibly supporting said first and second end members, wherein said end members each include a rod portion extending along said longitudinal axis and an end wall at an end of said rod portion, wherein at least one of said end walls includes an inner flange and an outer flange extending around said longitudinal axis and a space is formed between said inner and outer flanges with said bumper portion received in said space, said bumper portion including a side face extending between opposite end faces, said end walls engaging said end faces and overlapping at least a portion of said side face.

15. The connecting element of claim 14, wherein each of said end walls includes said inner flange and said outer flange forming said space with said bumper portion is in each of said spaces.

16. The connecting element of claim 15, wherein said bumper portion includes a wall extending about a central bore, said wall being received in said spaces defined between said inner flanges and said outer flanges, wherein said wall tapers toward said end members.

17. The connecting element of claim 15, wherein said rod portions each define an axial bore and further comprising a linking element in said axial bores, said linking element extending between opposite ends, said opposite ends being engaged to an outer end of a respective one of said rod portions remote from said end wall of said respective rod portion.

18. A method for assembling a connecting element for stabilizing a spinal column segment, comprising:
   providing a first end member with a first rod portion and a first end wall at an end of the first rod portion, the first rod portion including a bore extending therealong that opens at the first end wall;
   providing a second end member with a second rod portion and a second end wall at an end of the second rod portion, the second rod portion including a bore extending therealong that opens at the second end wall;
   providing a bumper assembly including a bumper portion with a central bore extending between opposite end faces of the bumper portion and a linking element extending through the central bore, the bumper portion including a side face; and positioning the linking element in the axial bores of each of the first and second rod portions and engaging the linking element to each of the first and second rod portions with the first and second end walls engaging the opposite end faces of the bumper portion, the first and second end walls overlapping at least a portion of the side face, and the rod portions lying along a longitudinal axis.

19. The method of claim 18, wherein the linking element is structured to collapse longitudinally when longitudinally compressed.

20. The method of claim 18, wherein the first and second rod portions and the bores thereof are curved along the longitudinal axis.

21. The method of claim 18, wherein the linking element is tensioned when engaged to the first and second rod portions and when the first and second end walls are engaged to the opposite end faces of the bumper portion.

22. The method of claim 18, wherein the linking element is slack when engaged to the first and second rod portions and when the first and second end walls are engaged to the opposite end faces of the bumper portion.

* * * * *